US009636101B2

(12) United States Patent
Wolf et al.

(10) Patent No.: US 9,636,101 B2
(45) Date of Patent: May 2, 2017

(54) BONE ANCHOR HAVING AN INTEGRATED STRESS ISOLATOR

(75) Inventors: Steven Wolf, Mission Viejo, CA (US); Vincent Tangherlini, Rancho Santa Margarita, CA (US); Norman S. Gordon, Irvine, CA (US)

(73) Assignee: ArthroCare Corporation, Austin, TX (US)

( * ) Notice: Subject to any disclaimer, the term of this patent is extended or adjusted under 35 U.S.C. 154(b) by 1237 days.

(21) Appl. No.: 13/602,941

(22) Filed: Sep. 4, 2012

(65) Prior Publication Data
US 2013/0060280 A1   Mar. 7, 2013

Related U.S. Application Data

(60) Provisional application No. 61/530,032, filed on Sep. 1, 2011.

(51) Int. Cl.
*A61F 2/08* (2006.01)
*A61B 17/04* (2006.01)
*A61B 90/00* (2016.01)

(52) U.S. Cl.
CPC .. *A61B 17/0401* (2013.01); *A61B 2017/0409* (2013.01); *A61B 2017/0414* (2013.01);
(Continued)

(58) Field of Classification Search
CPC ........ A61B 17/0401; A61B 2017/0414; A61B 2017/0445; A61B 2019/307;
(Continued)

(56) References Cited

U.S. PATENT DOCUMENTS 918,570 A    4/1909 Mather ................. 292/318
1,153,053 A  9/1915 Forster ................. 43/44.85
(Continued)

FOREIGN PATENT DOCUMENTS

DE   3509417      9/1986   ............ A61B 17/58
EP   0 535 906 A2 4/1993   ............ A61B 17/04
(Continued)

OTHER PUBLICATIONS

PCT Search Report and Written Opinion for PCT/US06/20657 7pgs, Mailed Oct. 2, 2007.
(Continued)

*Primary Examiner* — Melanie Tyson
*Assistant Examiner* — Rachel S Highland
(74) *Attorney, Agent, or Firm* — Norman F. Hainer, Jr.

(57) ABSTRACT

The present disclosure includes a knotless suture anchoring system for anchoring a suture with respect to a body cavity, including a bone anchor body with at least one rigid anchoring structure to secure the anchor body within the body cavity. The anchor body has a longitudinal bore and cross-pin extending across the bore. A retention member is coupled to the anchor body with a break notch therebetween, which may selectively fracture to separate the body from the retention member. Additionally there is a suture cutout on the retention member and a relief feature positioned along the break notch and approximately diametrically opposed from the suture cutout, the relief feature acting to alter the force dissipation along the break notch during the separation of the retention member from the anchor body.

17 Claims, 11 Drawing Sheets

(52) U.S. Cl.
CPC ............. *A61B 2017/0445* (2013.01); *A61B 2017/0451* (2013.01); *A61B 2017/0456* (2013.01); *A61B 2090/037* (2016.02); *A61F 2/0811* (2013.01); *A61F 2002/0817* (2013.01); *A61F 2002/0829* (2013.01); *A61F 2002/0841* (2013.01); *A61F 2002/0847* (2013.01); *A61F 2002/0852* (2013.01)

(58) Field of Classification Search
CPC .... A61B 2017/0451; A61B 2017/0456; A61B 2017/0409; A61F 2/0811; A61F 2002/0817; A61F 2002/0832; A61F 2002/0829; A61F 2002/0841; A61F 2002/0847; A61F 2002/0852
See application file for complete search history.

(56) References Cited

U.S. PATENT DOCUMENTS

| | | | | |
|---|---|---|---|---|
| 1,565,041 | A | 12/1925 | Arneu | 24/129 R |
| 2,269,963 | A | 1/1942 | Wrapler | 604/604 |
| 2,485,531 | A | 10/1949 | Dzus et al. | 128/92 |
| 2,600,395 | A | 6/1952 | Domoj et al. | 87/13 |
| 3,143,916 | A | 8/1964 | Rice | 85/71 |
| 3,716,058 | A | 2/1973 | Tanner, Jr. | |
| 3,942,407 | A | 3/1976 | Mortensen | 85/71 |
| 3,946,740 | A | 3/1976 | Bassett | 128/334 |
| 3,994,521 | A | 11/1976 | Van Gompel | 292/319 |
| 4,109,658 | A | 8/1978 | Hughes | 128/340 |
| 4,210,148 | A | 7/1980 | Stivala | 606/232 |
| 4,274,324 | A | 6/1981 | Giannuzzi | 411/38 |
| 4,301,551 | A | 11/1981 | Dore et al. | 623/13.3 |
| 4,319,428 | A | 3/1982 | Fox | 47/42 |
| 4,345,601 | A | 8/1982 | Fukuda | 128/339 |
| 4,373,530 | A | 2/1983 | Kilejian | 128/334 R |
| 4,384,389 | A | 5/1983 | Sato | 24/136 K |
| 4,409,974 | A | 10/1983 | Freedland | 128/92 |
| 4,456,270 | A | 6/1984 | Zettl et al. | 279/62 |
| 4,467,478 | A | 8/1984 | Jurgutis | 606/75 |
| 4,483,023 | A | 11/1984 | Hoffman, Jr. et al. | 623/13.15 |
| 4,493,323 | A | 1/1985 | Albright et al. | 128/340 |
| 4,580,936 | A | 4/1986 | Francis et al. | 411/38 |
| 4,590,928 | A | 5/1986 | Hunt et al. | 606/72 |
| 4,597,776 | A | 7/1986 | Ullman et al. | 48/197 R |
| 4,605,414 | A | 8/1986 | Czajka | 623/13.11 |
| 4,621,640 | A | 11/1986 | Mulhollan et al. | 128/340 |
| 4,635,637 | A | 1/1987 | Schreiber | 128/337 |
| 4,657,461 | A | 4/1987 | Smith | 411/340 |
| 4,672,957 | A | 6/1987 | Hourahane | 606/80 |
| 4,680,835 | A | 7/1987 | Horng | 24/712.5 |
| 4,712,542 | A | 12/1987 | Daniel et al. | 606/96 |
| 4,721,103 | A | 1/1988 | Freedland | 128/92 |
| 4,731,084 | A | 3/1988 | Dunn et al. | 623/13.19 |
| 4,738,255 | A | 4/1988 | Goble | |
| 4,741,330 | A | 5/1988 | Hayhurst | 123/43 R |
| 4,750,492 | A | 6/1988 | Jacobs | 606/230 |
| 4,772,286 | A | 9/1988 | Goble et al. | 623/13.14 |
| 4,779,616 | A | 10/1988 | Johnson et al. | 606/148 |
| 4,809,408 | A | 3/1989 | Abrahamson | 24/136 K |
| 4,823,780 | A | 4/1989 | Odensten et al. | 606/96 |
| 4,828,439 | A | 5/1989 | Giannuzzi | 411/37 |
| 4,851,005 | A | 7/1989 | Hunt et al. | 623/18 |
| 4,870,957 | A | 10/1989 | Goble et al. | 606/73 |
| 4,917,700 | A | 4/1990 | Aikins | 623/13.19 |
| 4,926,860 | A | 5/1990 | Stice et al. | 606/144 |
| 4,935,027 | A | 6/1990 | Yoon | 606/146 |
| 4,946,467 | A | 8/1990 | Ohi et al. | 606/228 |
| 4,946,468 | A | 8/1990 | Li | 606/232 |
| 4,957,498 | A | 9/1990 | Caspari | 606/146 |
| 4,968,315 | A | 11/1990 | Gatturna | 606/72 |
| 4,981,149 | A | 1/1991 | Yoon et al. | 128/898 |
| 4,987,665 | A | 1/1991 | Dumican | 28/218 |
| 5,002,550 | A | 3/1991 | Li | 606/139 |
| 5,019,093 | A | 5/1991 | Kaplan et al. | 606/228 |
| 5,037,422 | A | 8/1991 | Hayhurst | 606/72 |
| 5,046,513 | A | 9/1991 | Gatturna | 128/898 |
| 5,059,201 | A | 10/1991 | Asnis | 606/144 |
| 5,062,344 | A | 11/1991 | Gerker | 87/8 |
| 5,085,661 | A | 2/1992 | Moss | 606/139 |
| 5,147,166 | A | 9/1992 | Harker et al. | 411/29 |
| 5,195,542 | A | 3/1993 | Gazielly et al. | 60/244 |
| 5,203,787 | A | 4/1993 | Noblitt et al. | 606/232 |
| RE34,293 | E | 6/1993 | Goble et al. | 623/13.14 |
| 5,217,495 | A | 6/1993 | Kaplan et al. | 623/13.18 |
| 5,219,359 | A | 6/1993 | McQuilkin et al. | 606/232 |
| 5,224,946 | A | 7/1993 | Hayhurst | 606/72 |
| 5,258,016 | A | 11/1993 | DiPoto et al. | 606/232 |
| 5,263,984 | A | 11/1993 | Li | 623/13.18 |
| 5,275,176 | A | 1/1994 | Chandler | 606/242 |
| 5,304,184 | A | 4/1994 | Hathaway et al. | 606/144 |
| 5,306,290 | A | 4/1994 | Martins et al. | 606/232 |
| 5,324,308 | A | 6/1994 | Pierce | 606/232 |
| 5,326,205 | A | 7/1994 | Anspach, Jr. et al. | 411/43 |
| 5,330,442 | A | 7/1994 | Green | 606/232 |
| 5,330,468 | A | 7/1994 | Burkhart | 606/96 |
| 5,330,488 | A | 7/1994 | Goldrath | 606/148 |
| 5,336,240 | A | 8/1994 | Metzler | 606/232 |
| 5,354,298 | A | 10/1994 | Lee | 606/72 |
| 5,364,407 | A | 11/1994 | Poll | 606/139 |
| 5,376,118 | A | 12/1994 | Kaplan et al. | 623/23.72 |
| 5,383,905 | A | 1/1995 | Gold et al. | 606/232 |
| 5,405,352 | A | 4/1995 | Weston | 606/148 |
| 5,405,359 | A | 4/1995 | Pierce | 606/232 |
| 5,411,506 | A | 5/1995 | Goble | |
| 5,411,523 | A | 5/1995 | Goble | 606/232 |
| 5,413,579 | A | 5/1995 | Tom Du | 606/87 |
| 5,417,691 | A | 5/1995 | Hayhurst | 606/72 |
| 5,417,699 | A | 5/1995 | Klein et al. | 606/139 |
| 5,417,712 | A | 5/1995 | Whitaker et al. | 606/232 |
| 5,431,666 | A | 7/1995 | Sauer et al. | 606/139 |
| 5,441,508 | A | 8/1995 | Gazielly et al. | 606/151 |
| 5,445,167 | A | 8/1995 | Yoon et al. | 128/898 |
| 5,450,860 | A | 9/1995 | O'Connor | 606/224 |
| 5,454,823 | A | 10/1995 | Richardson et al. | 606/148 |
| 5,464,427 | A | 11/1995 | Curtis | |
| 5,470,335 | A | 11/1995 | DuToit | 606/73 |
| 5,472,452 | A | 12/1995 | Trott | 606/232 |
| 5,480,403 | A | 1/1996 | Lee et al. | 606/72 |
| 5,486,197 | A | 1/1996 | Le et al. | 606/232 |
| 5,499,991 | A | 3/1996 | Garman et al. | 606/148 |
| 5,501,683 | A | 3/1996 | Trott | 606/72 |
| 5,501,695 | A | 3/1996 | Anspach, Jr. et al. | 606/72 |
| 5,505,735 | A | 4/1996 | Li | 606/72 |
| 5,514,159 | A | 5/1996 | Matula et al. | 606/232 |
| 5,520,700 | A | 5/1996 | Beyar et al. | 606/139 |
| 5,522,820 | A | 6/1996 | Caspari et al. | 606/148 |
| 5,527,322 | A | 6/1996 | Klein et al. | 606/144 |
| 5,527,343 | A | 6/1996 | Bonutti | 606/232 |
| 5,531,763 | A | 7/1996 | Mastri et al. | 606/148 |
| 5,531,792 | A | 7/1996 | Huene | 623/16 |
| 5,534,012 | A | 7/1996 | Bonutti | 606/232 |
| 5,540,703 | A | 7/1996 | Barker, Jr. et al. | 606/139 |
| 5,545,180 | A | 8/1996 | Le et al. | 606/232 |
| 5,549,617 | A | 8/1996 | Green et al. | 606/144 |
| 5,549,630 | A | 8/1996 | Bonutti | 606/232 |
| 5,553,360 | A | 9/1996 | Lucas et al. | 24/136 K |
| 5,562,689 | A | 10/1996 | Green et al. | 606/151 |
| 5,569,305 | A | 10/1996 | Bonutti | 606/232 |
| 5,569,306 | A | 10/1996 | Thal | 606/232 |
| 5,571,104 | A | 11/1996 | Li | 606/72 |
| 5,571,120 | A | 11/1996 | Yoon | 606/148 |
| 5,573,540 | A | 11/1996 | Yoon | 606/139 |
| 5,573,542 | A | 11/1996 | Stevens | 606/144 |
| 5,573,548 | A | 11/1996 | Nazre et al. | 606/232 |
| 5,575,801 | A | 11/1996 | Habermeyer et al. | 606/148 |
| 5,584,835 | A | 12/1996 | Greenfield | 606/73 |
| 5,584,839 | A | 12/1996 | Gieringer | 606/96 |
| 5,584,860 | A | 12/1996 | Goble et al. | 606/232 |
| 5,584,862 | A | 12/1996 | Bonutti | 606/232 |
| 5,591,207 | A | 1/1997 | Coleman | 606/232 |
| 5,593,189 | A | 1/1997 | Little | 289/17 |
| 5,601,558 | A | 2/1997 | Torrie et al. | 606/72 |
| 5,609,597 | A | 3/1997 | Lehrer | 606/139 |

(56) References Cited

U.S. PATENT DOCUMENTS

| | | | | |
|---|---|---|---|---|
| 5,611,801 | A | 3/1997 | Songer | 606/73 |
| 5,613,974 | A | 3/1997 | Andreas et al. | 606/144 |
| 5,618,290 | A | 4/1997 | Toy et al. | 606/139 |
| 5,618,314 | A | 4/1997 | Harwin et al. | 606/232 |
| 5,626,614 | A | 5/1997 | Hart | 606/232 |
| 5,630,824 | A | 5/1997 | Hart | 606/139 |
| 5,632,748 | A | 5/1997 | Beck, Jr. et al. | 606/72 |
| 5,645,589 | A | 7/1997 | Li | 623/16 |
| 5,647,874 | A | 7/1997 | Hayhurst | 606/72 |
| 5,649,940 | A | 7/1997 | Hart et al. | 606/148 |
| 5,649,963 | A | 7/1997 | McDevitt | 606/232 |
| 5,658,313 | A | 8/1997 | Thal | 606/232 |
| 5,665,110 | A | 9/1997 | Chervitz et al. | 606/232 |
| 5,665,112 | A | 9/1997 | Thal | 606/232 |
| 5,667,528 | A | 9/1997 | Colligan | 606/224 |
| D385,352 | S | 10/1997 | Bales et al. | D24/145 |
| 5,681,333 | A | 10/1997 | Burkhart et al. | 606/148 |
| 5,681,351 | A | 10/1997 | Jamiolkowski | 606/232 |
| 5,683,418 | A | 11/1997 | Luscombe et al. | 606/232 |
| 5,683,419 | A | 11/1997 | Thal | 606/232 |
| 5,690,649 | A | 11/1997 | Li | 606/139 |
| 5,690,676 | A | 11/1997 | Di Poto | |
| 5,693,060 | A | 12/1997 | Martin | 606/148 |
| 5,697,950 | A | 12/1997 | Fucci et al. | 606/232 |
| 5,702,397 | A | 12/1997 | Goble | |
| 5,702,398 | A | 12/1997 | Tarabishy | 606/72 |
| 5,707,362 | A | 1/1998 | Yoon | 604/164 |
| 5,707,394 | A | 1/1998 | Miller et al. | 606/232 |
| 5,709,708 | A | 1/1998 | Thal | 606/232 |
| 5,720,765 | A | 2/1998 | Thal | 606/232 |
| 5,725,529 | A | 3/1998 | Nicholson et al. | 606/148 |
| 5,725,541 | A | 3/1998 | Anspach, III et al. | 606/151 |
| 5,728,136 | A | 3/1998 | Thal | 606/232 |
| 5,733,307 | A | 3/1998 | Dinsdale | 606/232 |
| 5,741,281 | A | 4/1998 | Martin | 606/148 |
| 5,741,282 | A | 4/1998 | Anspach, III et al. | 606/151 |
| 5,766,250 | A | 6/1998 | Chervitz et al. | 623/13 |
| 5,782,863 | A | 7/1998 | Bartlett | 606/232 |
| 5,782,864 | A | 7/1998 | Lizardi | 606/232 |
| 5,782,865 | A | 7/1998 | Grotz | 606/72 |
| 5,791,899 | A | 8/1998 | Sachdeva | 433/173 |
| 5,792,152 | A | 8/1998 | Klein et al. | 606/144 |
| 5,797,927 | A | 8/1998 | Yoon | 606/144 |
| 5,797,963 | A | 8/1998 | McDevitt | 606/232 |
| 5,810,848 | A | 9/1998 | Hayhurst | 606/144 |
| 5,810,854 | A | 9/1998 | Beach | 606/232 |
| 5,814,052 | A | 9/1998 | Nakao et al. | 606/148 |
| 5,814,071 | A | 9/1998 | McDevitt et al. | 606/232 |
| 5,814,072 | A | 9/1998 | Bonutti | 606/232 |
| 5,843,111 | A | 12/1998 | Vijfvinkel | 606/171 |
| 5,849,004 | A | 12/1998 | Bramlet | 606/232 |
| 5,860,978 | A | 1/1999 | McDevitt | 606/72 |
| 5,860,991 | A | 1/1999 | Klein et al. | 606/144 |
| 5,860,992 | A | 1/1999 | Daniel et al. | 606/145 |
| 5,868,789 | A | 2/1999 | Heubner | 606/232 |
| 5,879,372 | A | 3/1999 | Bartlett | 606/232 |
| 5,882,340 | A | 3/1999 | Yoon | 604/164 |
| 5,885,294 | A | 3/1999 | Pedlick et al. | 606/80 |
| 5,891,168 | A | 4/1999 | Thal | 606/232 |
| 5,893,850 | A | 4/1999 | Cachia | 606/72 |
| 5,902,311 | A | 5/1999 | Andreas et al. | 606/144 |
| 5,904,692 | A | 5/1999 | Steckel et al. | 606/139 |
| 5,911,721 | A | 6/1999 | Nicholson et al. | 606/72 |
| 5,921,994 | A | 7/1999 | Andreas et al. | 606/144 |
| 5,928,244 | A * | 7/1999 | Tovey | A61F 2/0805 606/104 |
| 5,935,107 | A | 8/1999 | Taylor et al. | 604/164 |
| 5,935,129 | A | 8/1999 | Mdevitt | 606/72 |
| 5,941,900 | A | 8/1999 | Bonutti | 606/232 |
| 5,941,901 | A | 8/1999 | Egan | 606/232 |
| 5,944,724 | A | 8/1999 | Lizardi | 606/104 |
| 5,944,739 | A | 8/1999 | Zlock et al. | 606/232 |
| 5,947,982 | A | 9/1999 | Duran | 606/139 |
| 5,948,000 | A | 9/1999 | Larsen et al. | 606/232 |
| 5,948,001 | A | 9/1999 | Larsen | 606/232 |
| 5,948,002 | A | 9/1999 | Bonutti | 606/232 |
| 5,957,953 | A | 9/1999 | DiPoto et al. | 606/232 |
| 5,957,968 | A | 9/1999 | Belden et al. | 607/126 |
| 5,961,530 | A | 10/1999 | Moore et al. | 606/148 |
| 5,961,538 | A | 10/1999 | Pedlick et al. | 606/232 |
| 5,968,044 | A | 10/1999 | Nicholson et al. | 606/72 |
| 5,980,558 | A | 11/1999 | Wiley | 606/232 |
| 5,980,559 | A | 11/1999 | Bonutti | 606/232 |
| 5,984,933 | A | 11/1999 | Yoon | 606/148 |
| 5,993,459 | A | 11/1999 | Larsen | 606/104 |
| 6,001,104 | A | 12/1999 | Benderev et al. | 606/80 |
| 6,001,109 | A | 12/1999 | Kontos | 606/148 |
| 6,007,566 | A | 12/1999 | Wenstrom | 606/232 |
| 6,007,567 | A | 12/1999 | Bonutti | 606/232 |
| 6,010,525 | A | 1/2000 | Bonutti et al. | 606/232 |
| 6,013,083 | A | 1/2000 | Bennett | 606/104 |
| 6,017,346 | A | 1/2000 | Grotz | 606/72 |
| 6,022,360 | A | 2/2000 | Reimels et al. | 606/144 |
| 6,022,373 | A | 2/2000 | Li | 606/232 |
| 6,024,758 | A | 2/2000 | Thal | 606/232 |
| 6,033,430 | A | 3/2000 | Bonutti | 606/232 |
| 6,036,699 | A | 3/2000 | Andreas et al. | 606/139 |
| 6,045,571 | A | 4/2000 | Hill et al. | 606/228 |
| 6,045,572 | A | 4/2000 | Johnson et al. | 606/232 |
| 6,045,573 | A | 4/2000 | Wenstrom et al. | 606/232 |
| 6,045,574 | A | 4/2000 | Thal | 606/232 |
| 6,048,351 | A | 4/2000 | Gordon et al. | 606/144 |
| 6,051,006 | A | 4/2000 | Shluzas et al. | 606/148 |
| 6,053,935 | A | 4/2000 | Brenneman et al. | 606/232 |
| 6,056,773 | A | 5/2000 | Bonutti | 606/232 |
| 6,066,146 | A | 5/2000 | Carroll et al. | 606/148 |
| 6,066,160 | A | 5/2000 | Colvin et al. | 606/232 |
| 6,068,648 | A | 5/2000 | Cole et al. | 606/232 |
| 6,086,608 | A | 7/2000 | Elk et al. | 606/232 |
| 6,096,051 | A | 8/2000 | Kortenbach et al. | 606/144 |
| 6,102,934 | A | 8/2000 | Li | 606/232 |
| 6,117,160 | A | 9/2000 | Bonutti | 606/215 |
| 6,117,161 | A | 9/2000 | Li | 606/232 |
| 6,143,004 | A | 11/2000 | Davis et al. | 606/144 |
| 6,146,386 | A | 11/2000 | Blackman | 606/103 |
| 6,146,406 | A | 11/2000 | Shluzas et al. | 606/232 |
| 6,149,669 | A | 11/2000 | Li | 606/232 |
| 6,156,039 | A | 12/2000 | Thal | 606/72 |
| 6,156,056 | A | 12/2000 | Kearns et al. | 606/232 |
| 6,159,235 | A | 12/2000 | Kim | 606/232 |
| 6,162,537 | A | 12/2000 | Martin et al. | 428/373 |
| 6,171,317 | B1 | 1/2001 | Jackson et al. | 606/148 |
| 6,200,329 | B1 | 3/2001 | Fung et al. | 606/232 |
| 6,200,893 | B1 | 3/2001 | Sneh | 438/685 |
| 6,206,895 | B1 | 3/2001 | Levison | 606/144 |
| 6,217,592 | B1 | 4/2001 | Freda et al. | 606/145 |
| 6,221,107 | B1 | 4/2001 | Steiner et al. | 623/13.14 |
| 6,228,096 | B1 | 5/2001 | Marchand | 606/139 |
| 6,241,736 | B1 | 6/2001 | Sater | 606/104 |
| 6,267,766 | B1 | 7/2001 | Burkhart | 606/72 |
| 6,280,474 | B1 | 8/2001 | Cassidy et al. | 623/16.11 |
| 6,293,961 | B2 | 9/2001 | Schwartz | 606/232 |
| 6,295,700 | B1 | 10/2001 | Plzak | 24/134 R |
| 6,315,781 | B1 | 11/2001 | Reinhardt | 606/108 |
| 6,319,252 | B1 | 11/2001 | McDevitt et al. | 606/60 |
| 6,319,269 | B1 | 11/2001 | Li | 606/232 |
| 6,319,271 | B1 | 11/2001 | Schwartz | 606/232 |
| 6,328,758 | B1 | 12/2001 | Tornier et al. | 606/232 |
| 6,355,053 | B1 | 3/2002 | Li | 606/232 |
| 6,409,743 | B1 | 6/2002 | Fenton | 606/232 |
| 6,432,123 | B2 | 8/2002 | Schwartz et al. | 606/232 |
| 6,436,109 | B1 | 8/2002 | Kontes | 606/148 |
| 6,451,030 | B2 | 9/2002 | Li et al. | 606/139 |
| 6,464,713 | B2 | 10/2002 | Bonutti | 606/232 |
| 6,468,293 | B2 | 10/2002 | Bonutti et al. | 606/232 |
| 6,471,715 | B1 | 10/2002 | Weiss | 606/216 |
| 6,475,230 | B1 | 11/2002 | Bonutti et al. | 606/232 |
| 6,491,714 | B1 | 12/2002 | Bennett | 606/232 |
| 6,517,542 | B1 | 2/2003 | Papay et al. | 606/73 |
| 6,520,980 | B1 | 2/2003 | Foerster | 606/232 |
| 6,524,317 | B1 | 2/2003 | Ritchart et al. | 606/72 |
| 6,527,794 | B1 | 3/2003 | McDevitt et al. | 606/232 |
| 6,540,770 | B1 | 4/2003 | Tornier et al. | 606/232 |
| 6,569,187 | B1 | 5/2003 | Bonutti et al. | 606/232 |

(56) References Cited

U.S. PATENT DOCUMENTS

| | | | |
|---|---|---|---|
| 6,575,987 B2 | 6/2003 | Gellman et al. | 606/151 |
| 6,582,453 B1 | 6/2003 | Tran et al. | 606/232 |
| 6,585,730 B1 | 7/2003 | Foerster | 606/232 |
| 6,635,073 B2 | 10/2003 | Bonutti | 606/232 |
| 6,638,279 B2 | 10/2003 | Bonutti | 606/60 |
| 6,645,227 B2 | 11/2003 | Fallin et al. | 606/232 |
| 6,648,903 B1 | 11/2003 | Pierson | |
| 6,652,561 B1 | 11/2003 | Tran | 606/232 |
| 6,656,183 B2 | 12/2003 | Colleran | |
| 6,660,008 B1 | 12/2003 | Foerster et al. | 606/72 |
| 6,660,023 B2 | 12/2003 | McDevitt et al. | 606/232 |
| 6,673,094 B1 | 1/2004 | McDevitt et al. | 606/232 |
| 6,679,896 B2 | 1/2004 | Gellman et al. | 606/148 |
| 6,682,549 B2 | 1/2004 | Bartlett | 606/232 |
| 6,689,154 B2 | 2/2004 | Bartlett | 606/232 |
| 6,692,516 B2 | 2/2004 | West et al. | 606/232 |
| 6,736,829 B1 | 5/2004 | Li et al. | 606/232 |
| 6,770,076 B2 | 8/2004 | Foerster | 606/72 |
| 6,780,198 B1 | 8/2004 | Gregoire et al. | 606/232 |
| 6,855,157 B2 | 2/2005 | Foerster et al. | 606/232 |
| 6,860,887 B1 | 3/2005 | Frankie | 606/104 |
| 6,887,259 B2 | 5/2005 | Lizardi | 606/232 |
| 6,939,379 B2 | 9/2005 | Sklar | 623/13.14 |
| 6,972,027 B2 | 12/2005 | Fallin et al. | 606/232 |
| 7,083,638 B2 | 8/2006 | Foerster | 606/232 |
| 7,087,064 B1 | 8/2006 | Hyde | 606/142 |
| 7,090,690 B2 | 8/2006 | Foerster | |
| 7,104,999 B2 | 9/2006 | Overaker | 606/142 |
| 7,144,415 B2 | 12/2006 | Del Rio et al. | 606/232 |
| 7,150,750 B2 | 12/2006 | Damarati | 623/17.11 |
| 7,150,757 B2 | 12/2006 | Fallin et al. | 606/232 |
| 7,247,164 B1 | 7/2007 | Ritchart et al. | 606/232 |
| 7,320,701 B2 | 1/2008 | Haut et al. | 606/232 |
| 7,322,978 B2 * | 1/2008 | West, Jr. | A61B 17/0401 411/308 |
| 7,329,272 B2 | 2/2008 | Burkhart et al. | 606/232 |
| 7,381,213 B2 | 6/2008 | Lizardi | 606/232 |
| 7,410,489 B2 | 8/2008 | Dakin et al. | 606/103 |
| 7,556,640 B2 | 7/2009 | Foerster | 606/232 |
| 7,588,587 B2 | 9/2009 | Barbieri et al. | 606/232 |
| 7,615,061 B2 | 11/2009 | White et al. | 606/148 |
| 7,637,926 B2 | 12/2009 | Foerster et al. | 606/232 |
| 7,674,274 B2 | 3/2010 | Foerster et al. | 606/232 |
| 7,682,374 B2 | 3/2010 | Foerster | 606/72 |
| 7,695,494 B2 | 4/2010 | Foerster | 606/232 |
| 7,837,710 B2 | 11/2010 | Lombardo et al. | 606/232 |
| 7,867,251 B2 | 1/2011 | Colleran et al. | 606/232 |
| 7,938,847 B2 | 5/2011 | Fanton et al. | 606/232 |
| 7,959,650 B2 * | 6/2011 | Kaiser | A61B 17/0401 606/232 |
| 7,963,972 B2 | 6/2011 | Foerster et al. | 606/139 |
| 7,981,140 B2 | 7/2011 | Burkhart | 606/232 |
| 8,109,966 B2 | 2/2012 | Ritchart et al. | 606/232 |
| 8,133,258 B2 | 3/2012 | Foerster et al. | 606/232 |
| 8,137,381 B2 | 3/2012 | Foerster et al. | 606/232 |
| 8,317,829 B2 | 11/2012 | Foerster et al. | 606/232 |
| 8,343,186 B2 | 1/2013 | Dreyfuss et al. | |
| 8,425,536 B2 | 4/2013 | Foerster et al. | 606/232 |
| 8,444,672 B2 | 5/2013 | Foerster | 606/232 |
| 8,623,052 B2 | 1/2014 | Dreyfuss et al. | |
| 8,657,854 B2 | 2/2014 | Foerster | 606/232 |
| 8,685,060 B2 | 4/2014 | Foerster | 606/232 |
| 8,801,755 B2 | 8/2014 | Dreyfuss et al. | |
| 8,821,541 B2 | 9/2014 | Dreyfuss et al. | |
| 9,023,083 B2 | 5/2015 | Foerster et al. | 606/139 |
| 9,034,014 B2 | 5/2015 | Catania et al. | 606/232 |
| 9,179,907 B2 | 11/2015 | ElAttrache et al. | |
| 2002/0052629 A1 | 5/2002 | Morgan | |
| 2002/0111653 A1 | 8/2002 | Foerster | |
| 2003/0065361 A1 | 4/2003 | Dreyfuss | |
| 2003/0105489 A1 | 6/2003 | Eichhorn et al. | 606/232 |
| 2003/0109900 A1 * | 6/2003 | Martinek | A61B 17/0401 606/219 |
| 2003/0167062 A1 | 9/2003 | Gambale | 606/232 |
| 2003/0195563 A1 | 10/2003 | Foerster | 606/232 |
| 2003/0195564 A1 | 10/2003 | Tran et al. | 606/232 |
| 2004/0133239 A1 | 7/2004 | Singhatat | 606/232 |
| 2004/0138683 A1 | 7/2004 | Shelton et al. | 606/151 |
| 2004/0138706 A1 | 7/2004 | Abrams et al. | 606/232 |
| 2004/0153074 A1 | 8/2004 | Bojarski et al. | 606/232 |
| 2004/0236336 A1 | 11/2004 | Foerster et al. | 606/72 |
| 2005/0033364 A1 | 2/2005 | Gregoire et al. | 606/232 |
| 2005/0055052 A1 * | 3/2005 | Lombardo | A61B 17/0401 606/232 |
| 2005/0080455 A1 | 4/2005 | Schmieding et al. | 606/232 |
| 2005/0090827 A1 | 4/2005 | Gedebou | 606/72 |
| 2005/0273101 A1 | 12/2005 | Schumacher | 606/61 |
| 2005/0277986 A1 | 12/2005 | Foerster | 606/232 |
| 2006/0004364 A1 | 1/2006 | Green et al. | 606/72 |
| 2006/0074422 A1 | 4/2006 | Story et al. | 606/142 |
| 2006/0079904 A1 | 4/2006 | Thal | 606/72 |
| 2006/0106423 A1 | 5/2006 | Weisel et al. | 606/232 |
| 2006/0161159 A1 | 7/2006 | Dreyfuss et al. | 606/72 |
| 2006/0271060 A1 | 11/2006 | Gordon | 606/232 |
| 2006/0271105 A1 | 11/2006 | Foerster | 606/232 |
| 2006/0282081 A1 | 12/2006 | Fanton et al. | 606/232 |
| 2007/0055379 A1 | 3/2007 | Stone et al. | 606/75 |
| 2007/0142838 A1 | 6/2007 | Jordan | 606/75 |
| 2007/0156148 A1 | 7/2007 | Fanton et al. | 606/72 |
| 2007/0276437 A1 | 11/2007 | Call et al. | 606/232 |
| 2008/0051836 A1 * | 2/2008 | Foerster | A61B 17/0401 606/232 |
| 2008/0119849 A1 | 5/2008 | Beardsley et al. | 606/61 |
| 2009/0069823 A1 | 3/2009 | Foerster et al. | 606/103 |
| 2009/0222040 A1 | 9/2009 | Foerster et al. | 606/232 |
| 2009/0222041 A1 | 9/2009 | Foerster et al. | 606/232 |
| 2009/0248068 A1 | 10/2009 | Lombardo et al. | 606/232 |
| 2010/0121348 A1 * | 5/2010 | van der Burg | A61B 17/0401 606/139 |
| 2010/0179573 A1 * | 7/2010 | Levinsohn | A61B 17/0401 606/145 |
| 2010/0191283 A1 | 7/2010 | Foerster et al. | 606/232 |
| 2011/0178560 A1 * | 7/2011 | Butler | A61B 17/7086 606/86 A |
| 2012/0158052 A1 | 6/2012 | Foerster et al. | 606/232 |
| 2013/0197575 A1 | 8/2013 | Karapetian et al. | 606/232 |
| 2013/0197576 A1 | 8/2013 | Catania et al. | 606/232 |
| 2013/0197577 A1 | 8/2013 | Wolf et al. | 606/232 |
| 2013/0197578 A1 | 8/2013 | Gregoire et al. | 606/232 |
| 2013/0197579 A1 | 8/2013 | Foerster et al. | 606/232 |
| 2013/0267998 A1 | 10/2013 | Vijay et al. | 606/232 |
| 2014/0207189 A1 | 7/2014 | Foerster et al. | 606/232 |
| 2015/0223926 A1 | 8/2015 | Foerster et al. | A61F 2/0811 |

FOREIGN PATENT DOCUMENTS

| | | | |
|---|---|---|---|
| EP | 0 571 686 A1 | 12/1993 | A61B 2/08 |
| EP | 0 611557 A2 | 8/1994 | A61B 2/08 |
| EP | 1 072 234 A2 | 1/2001 | A61F 2/08 |
| EP | 1 072 237 A1 | 1/2001 | A61F 2/36 |
| FR | 2777442 | 10/1999 | A61B 17/04 |
| FR | 2777447 | 10/1999 | A61B 17/56 |
| JP | 2286468 | 11/1990 | B62D 1/16 |
| JP | 8-52154 | 2/1996 | A61B 17/56 |
| JP | 08-206121 | 8/1996 | A61B 17/04 |
| JP | 11-502437 | 3/1999 | A61B 17/58 |
| JP | 2000-225118 | 8/2000 | A61B 17/04 |
| WO | 89/10096 | 11/1989 | A61B 19/00 |
| WO | 91/06247 | 5/1991 | A61B 17/00 |
| WO | 95/06439 | 3/1995 | A61B 17/00 |
| WO | 95/25469 | 9/1995 | A61B 17/04 |
| WO | 96/28118 | 9/1996 | A61F 5/00 |
| WO | 97/20522 | 6/1997 | A61F 2/08 |
| WO | 99/53843 | 10/1999 | A61B 17/04 |
| WO | 99/53844 | 10/1999 | A61B 17/04 |
| WO | 02/21997 | 3/2002 | A61B 17/04 |
| WO | 03/020137 | 3/2003 | A61B 17/02 |

(56) References Cited

FOREIGN PATENT DOCUMENTS

| WO | 03/049620 | 6/2003 | ............ A61B 17/04 |
| WO | 2011/060437 | 5/2011 | ............ A61B 17/04 |

OTHER PUBLICATIONS

PCT Search Report and Written Opinion for PCT/US06/21125 6pgs, Mailed May 22, 2008.
PCT International Search Report for PCT/US01/21905 3pgs, Mailed Jan. 22, 2002.
PCT International Preliminary Examination Report for PCT/US01/21905 3pgs, Oct. 17, 2003.
PCT International Search Report for PCT/US01/17689 3pgs, Mailed Dec. 19, 2001.
PCT International Preliminary Examination Report for PCT/US01/17689 15pgs, Feb. 9, 2003.
PCT International Search Report for PCT/US02/17493 1pg, Mailed Mar. 27, 2003.
PCT International Preliminary Examination Report for PCT/US02/17493 4pgs, Sep. 8, 2003.
PCT International Search Report for PCT/US02/41018 2pgs, Mailed Jun. 5, 2003.
PCT International Preliminary Examination Report for PCT/US02/41018 3pgs, Feb. 22, 2004.
PCT International Search Report for PCT/US02/04231 1pg, Mailed Aug. 14, 2002.
PCT International Preliminary Examination Report for PCT/US02/04231 3pgs, Nov. 13, 2002.
PCT International Search Report for PCT/US03/35695 1 pg, Mailed Feb. 14, 2005.
PCT International Preliminary Examination Report for PCT/US03/35695 4pgs, Dec. 21, 2005.
EP Partial European Search Report for EP02742470 3pgs, Apr. 13, 2004.
EP Supplementary European Search Report for EP02742470 5pgs, Jul. 30, 2004.
EP Extended Search Report for EP09162639 4pgs, Oct. 28, 2009.
EP Supplementary European Search Report for EP02792506 3pgs, Mar. 24, 2010.
UK Search Report for GB 0816111.9 3pgs, Dec. 16, 2008.
European Search Report for EP 02734649 3pgs, Jan. 22, 2009.
DE Examination Report for DE 102008046561.5 11 pgs, Nov. 16, 2012.

* cited by examiner

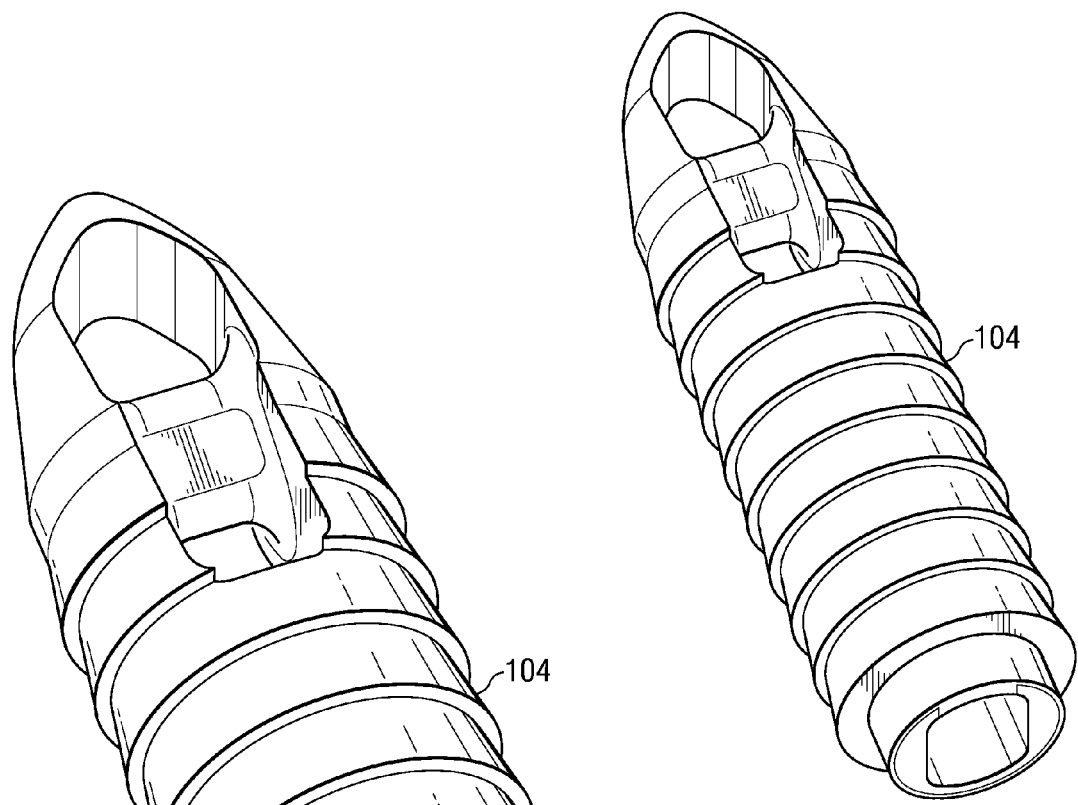
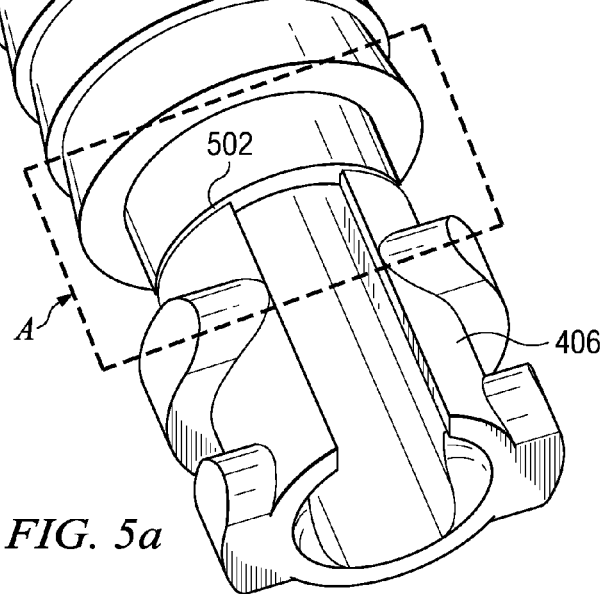
FIG. 5c
FIG. 5a

BONE ANCHOR HAVING AN INTEGRATED STRESS ISOLATOR

CROSS-REFERENCE TO RELATED APPLICATIONS

This application claims the benefit under 35 U.S.C. §119(e) of U.S. Provisional Application No. 61/530,032 filed Sep. 1, 2011, the complete disclosure of which is hereby incorporated by reference in its entirety for all purposes.

FIELD OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

BACKGROUND

A bone anchor may be used to attach soft tissue to bone and, more specifically, to secure connective tissue, such as ligaments or tendons, to bone. For example, a suture may be passed through the connective tissue and attached to the bone anchor, which is then placed within a borehole or cavity in the bone proximate to the connective tissue. This provides a site for the sutured connective tissue to be drawn towards.

A practitioner may utilize an applicator, which is attached to the bone anchor (e.g., by grasping a retention member coupled to the bone anchor), to properly position the bone anchor in the bone. The practitioner detaches the applicator from the bone anchor when the bone anchor is properly positioned. Detaching the applicator from the bone anchor may be through the application of an axial force to the bone anchor, causing the bone anchor to shear or fracture from the feature grasped by the applicator. In some cases, the bone anchor is fabricated from a polymer, such as polyether ether ketone (PEEK), and thus may be damaged by forces generated during its separation from the feature grasped by the applicator.

SUMMARY

The present disclosure presents an improved knotless anchoring system for attaching soft tissue to bone. The apparatus generally includes a bone anchor, an applicator system for inserting the bone anchor into a body cavity such as a bone tunnel and a length of suture for coupling both with the soft tissue and then with the bone anchor.

In one aspect a knotless suture system is disclosed for attaching soft tissue to a body cavity, with the system including a bone anchor body having at least one rigid anchoring structure to secure the anchor body within the body cavity and a longitudinal bore extending through the anchor body and a cross-pin extending laterally across the longitudinal bore. The system may also have a retention member coupled to the anchor body and a suture plug for placement in the longitudinal bore to frictionally secure at least one length of suture within the longitudinal bore. Between the anchor body and the retention member there is a break notch that may selectively fracture, upon the application of a load on the body anchor, so as to facilitate separation of the anchor body from the retention member.

The retention member may also have a suture cutout disposed along the break notch, so as to interrupt the line of the break notch. This cutout enables the length of suture to enter and exit the longitudinal bore after being passed around the cross-pin; without disrupting other components of the system. The line of the break notch may also be interrupted by a relief feature, positioned along the break notch and approximately diametrically opposed from the suture cutout.

In another aspect a method of securing soft tissue with respect to a body cavity without knots is disclosed, the method including passing a length of suture through soft tissue so that a portion of the suture is secured in the soft tissue, resulting in at least one free end. A bone anchor body is then provided, the body having longitudinal bore with an opening at the proximal end and an inner wall, with a cross-pin extending across the longitudinal bore towards the distal end of the body. A free end of the suture may then be passed through a suture cutout of a retention member coupled to the anchor body, such that the suture extends into the longitudinal bore, around the cross-pin, and exits the longitudinal bore through the suture cutout. The bone anchor body may then be inserted into the body cavity, which may be previously prepared for receiving the anchor body. Tension may then be applied to the suture between the tissue and the bone anchor, so as to better position the tissue with respect to the bone. Once the correct tension is achieved, a suture plug may be inserted into the longitudinal bore to secure the suture to the inner wall of the longitudinal bore and an axial force may be applied via the suture plug to the bone anchor body so that the bone anchor body separates from the retention member along a break notch located between the bone anchor body and the retention member. During this separation, the propogation of forces may be dissipated or altered by a relief feature that is positioned along the break notch approximately diametrically opposed from the suture cutout.

In another aspect of the disclosure, a knotless suture anchoring system for anchoring a length of suture with respect to a body cavity is disclosed, with the system including a bone anchor body applicator and a bone anchor body. The body may have at least one rigid anchoring structure to secure the bone anchor body within the body cavity, as well as a longitudinal bore and a cross-pin extending laterally through the longitudinal bore. The system may also include a retention member coupled to the bone anchor body and engaged with the bone anchor body applicator. There may also be a suture plug for placement in the longitudinal bore to frictionally secure a suture to the inner wall of the longitudinal bore and a suture plug driver rod, in communication with the suture plug and disposed coaxially within the retention member. The bone anchor and retention member may be selectively separated via a break notch disposed between the bone anchor body and the retention member, the break notch creating a weakened coupling between the body and member so that it may fracture. The retention member may also have a suture cutout that is located so as to be in communication with the break notch. This cutout allows the suture to enter and exit the longitudinal bore after being passed around the cross-pin without interrupting the motion of the driver rod. There may also be a relief feature positioned along the break notch and approximately diametrically opposed from the suture cutout.

The invention, together with additional features and advantages thereof, may best be understood by reference to the following description taken in conjunction with the accompanying illustrative drawing

BRIEF DESCRIPTION OF THE DRAWINGS

For a detailed description of exemplary embodiments, reference will now be made to the accompanying drawings in which:

FIG. 5a shows another view of a bone anchor comprising a break notch in accordance with various embodiments;

FIG. 5c shows a bone anchor after separation from a retention member in accordance with various embodiments;

NOTATION AND NOMENCLATURE

Figure 1:
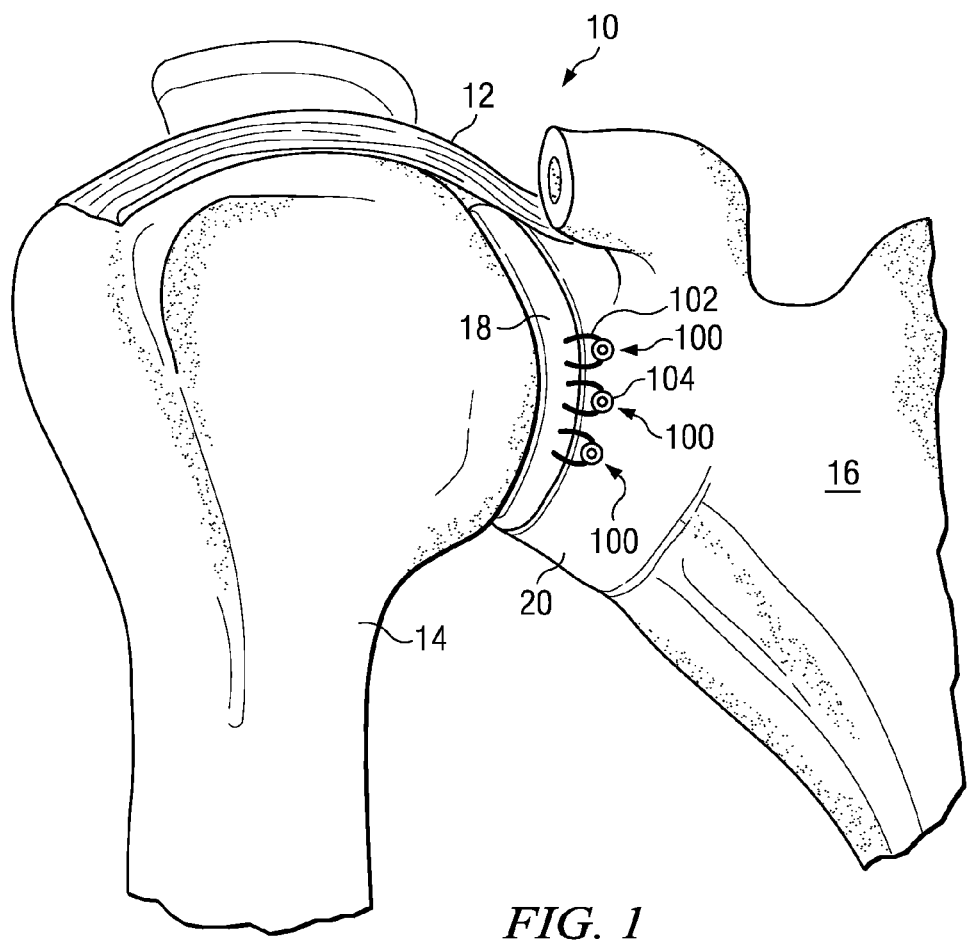
FIG. 1 shows a partial view of the shoulder anatomy in which the humorous is adjacent to the rotator cuff and labrum as it nests within and against the glenoid and anchors placed in the labrum in accordance with various embodiments.

Certain terms are used throughout the following description and claims to refer to particular system components. As one skilled in the art will appreciate, companies that design and manufacture medical devices may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. Further, the terms "proximal" and distal are intended to refer to proximity relative to a bone anchor applicator. Thus, if a first device is distal and a second device is proximal, the second device is nearer to the bone anchor applicator than the first device.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

In accordance with various embodiments, a bone anchor comprising a relief feature reduces or eliminates the likelihood of failure during separation from an applicator. The relief feature may be positioned between the bone anchor and a retention member that is grasped or held by the applicator. The retention member may comprise a suture cutout, which acts as a port for a suture to enter and exit the bone anchor. In some cases, the relief feature may be approximately equidistant and opposite from the suture cutout to dissipate force vectors or "fracture fronts" as they travel around the circumference of the bone anchor from the suture cutout, where separation between the bone anchor and the relief member is likely to initiate. Dissipation of the fracture fronts reduces or eliminates the chance of a fracture or failure in the bone anchor, particularly at a point approximately equidistant and oppose from the suture cutout, or where the separation between the bone anchor and the retention member begins.

FIG. 1 illustrates a partial view of the shoulder anatomy 10 in which the humerus 14 is adjacent to the rotator cuff 12 and labrum 18 as it nests within and against the glenoid 20. The scapula 16 is partially shown. For clarity, various bones and other soft tissue are not illustrated in FIG. 1.

FIG. 1 also illustrates exemplary placement of anchors 100 according to the system described herein. As shown, the anchor 100 secures soft tissue (e.g., the labrum 18) to hard tissue (e.g., the glenoid) via a suture 102. Any number of anchors 100 may be employed. Moreover, the location of the anchors and sutures may vary as required. As shown, the anchor body 104 is located within a cavity in the bone. This cavity is created prior to affixing the anchor within the bone.

Figure 2:
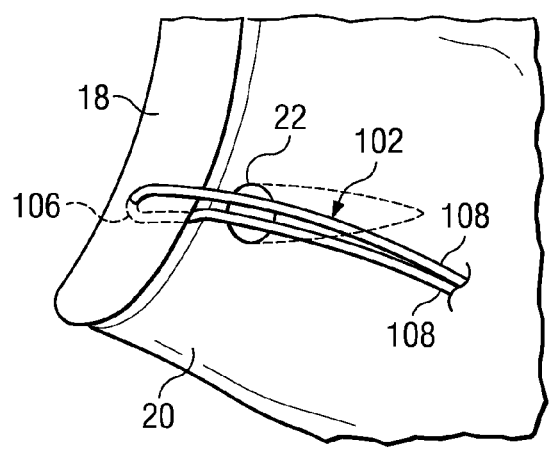
FIG. 2 shows a suture within the labrum and adjacent to a cavity created in the bone in accordance with various embodiments.

FIG. 2 shows a view of a single suture 102 adjacent to a cavity 22 created in the bone. At this point, the free ends 108 of the suture 102 do not enter the cavity but are directed towards the bone anchor (not shown) as described in further detail below. FIG. 2 illustrates placement of the suture 102 within the labrum 18. In this example, a looping section 106 secures the suture 102 to the labrum 18. The looping section 106 may extend through the tissue so that both free ends 108 of the suture 102 can be loaded into the bone anchor.

Figure 3:
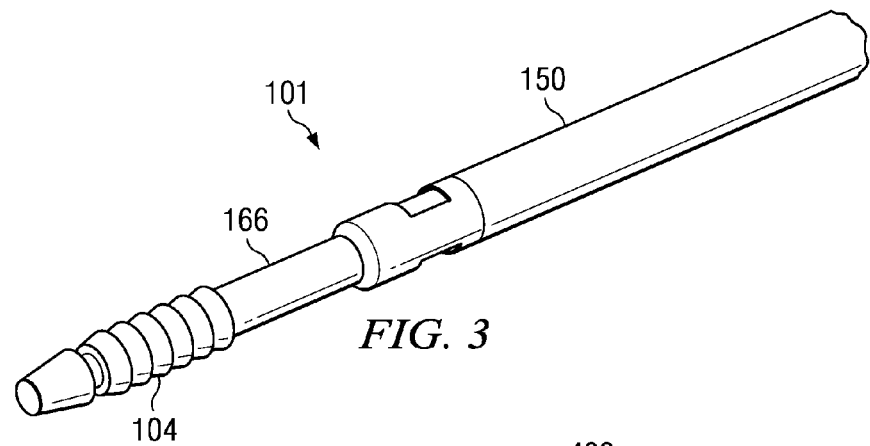
FIG. 3 shows a perspective view of a bone anchor coupled to a bone anchor applicator in accordance with various embodiments.

FIG. 3 illustrates a knotless suture system 101 upon deployment, including a bone anchor body 104 coupled to an applicator system 150. The free end of the suture 108 (not shown in FIG. 3) engages the bone anchor body 104, which will be described in further detail below, and the looping section 106 of the suture is secured to, for example, the labrum (also not shown in FIG. 3). The bone anchor body 104 may include ridges as shown, or another suitable rigid anchoring structure, to anchor the bone anchor body 104 to bone. The ridges are tapered to permit insertion of the anchor body 104 into bone when advanced into the bone but resist removal from the bone. FIG. 3 illustrates the bone anchor body 104 prior to being disengaged from the applicator system 150. As shown, a grasping member 166 grasps a profile of a retention member (described later) coupled to the anchor body 104 to secure the bone anchor body 104 to the applicator system 150.

Figure 4A:
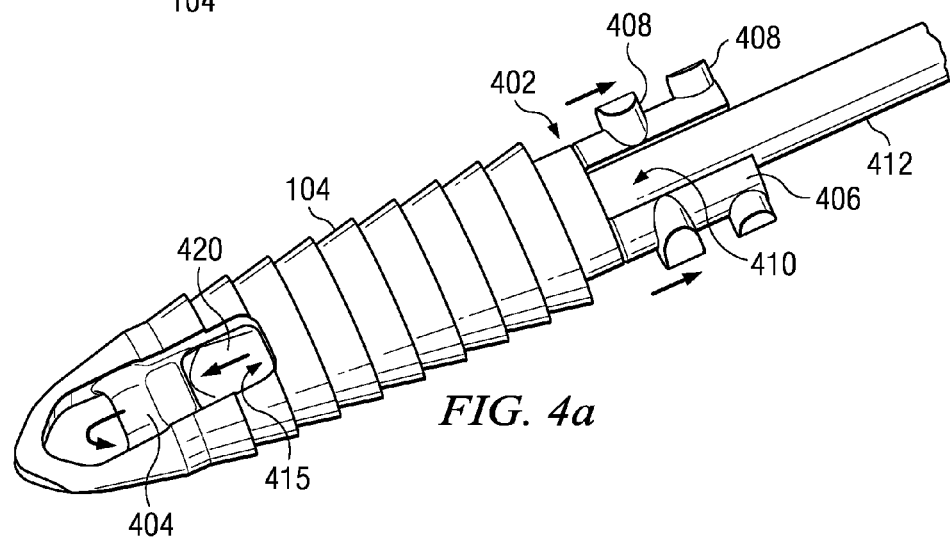
FIG. 4a shows a bone anchor coupled to a retention member and a portion of a bone anchor applicator in accordance with various embodiments.

FIG. 4a illustrates an anchor body 104 in further detail. The bone anchor body 104 comprises a longitudinal bore 415 that the suture 102 may pass through (suture not shown in this figure). The suture 102 enters the bore 415 at the bone anchor body proximal end 402, travels distally through the longitudinal bore 415, loops around a cross-pin 404 that extends laterally across the longitudinal bore 415 toward the distal end of the anchor body 104, and exits out of the proximal end 402. As shown, the bone anchor body 104 is coupled to a retention member 406 at the proximal end 402, and the retention member includes lugs 408 and a suture cutout 410. The lugs 408 may be grasped or engaged by matching relief sections of a grasping member 166 (not shown) and are operable to secure the retention member 406 to the grasping member 166, and therefore connect the bone anchor body 104 to the applicator system 150 (not shown here). The suture cutout 410 provides an entry and exit path for the lengths of suture 102 when the bone anchor body 104 is grasped by the applicator system 150, via the grasping member 166. The length of suture 102 may be tensioned by a practitioner. Once a desired tension is achieved, a suture plug 420 may be driven into the longitudinal bore 415 by a rod 412, coaxially situated inside the grasping member 166 and retention member 406. The rod 412 may be removably attached from suture plug 420. Suture plug 420 may also aid in disengaging the anchor body 104 from the applicator system 150, as the plug 420 may be driven distally so that the plug distal tip may bear upon a proximal surface of cross pin 404, as shown in FIG. 4a. This may transfer a tensile load to a weakened portion of the bone anchor body 104, as will be described later, allowing said weakened portion to be controllably fractured and thereby disconnect the anchor body 104 from the retention member 406. Cross-pin 404 proximal surface and the tip of suture plug 420 may therefore be cooperatively shaped so as to mate with each other effectively for this purpose, i.e. the mating surfaces may have a substantial area of flat surface to apply an even load over the area.

Figure 4B:
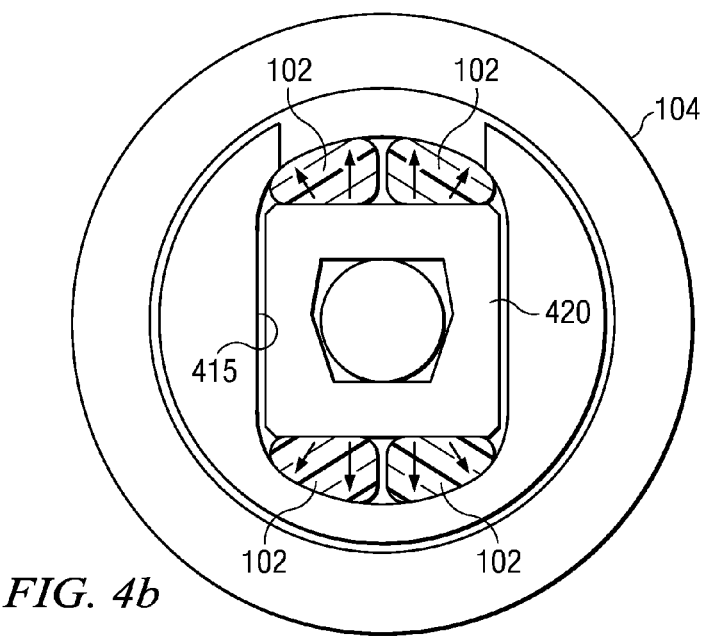
FIG. 4b shows an radial cross section of a bone anchor with a suture plug and sutures in accordance with various embodiments.

FIG. 4b shows a radial cross section of the bone anchor body 104 with a suture plug 420 inserted in the longitudinal bore 415. One pair of suture legs are, for example, "entering" (i.e., coming from the looping section 106 of the suture secured to the labrum) the longitudinal bore 415 while the other pair of suture legs are "exiting" the longitudinal bore 415 after looping around the cross-pin 404 (not shown). As explained above, once a desired tension of the suture 102 is achieved, the suture plug 420 is driven into the longitudinal bore 415. The suture plug 420 wedges the suture 102 against opposing internal walls of the bore 415, providing for a knotless suture lock to the bone anchor body 104. The suture plug 420 will remain within the anchor body 104, in vivo, and is shown to be approximately square shaped. In general, suture plug 420 and bore 415 are both cooperatively shaped so as to create a frictional fit between the suture legs 102, the plug 420 and the bore 415 i.e. to wedge the suture legs 102 in place and keep the plug 420 in place while in vivo. The arrows in FIG. 4b indicate the stresses on bone anchor body 104 with plug 420 wedged within bore 415. The suture legs 102 enter and exit the longitudinal bore 415 through the suture cutout 410 of the retention member 406.

Figure 5B:
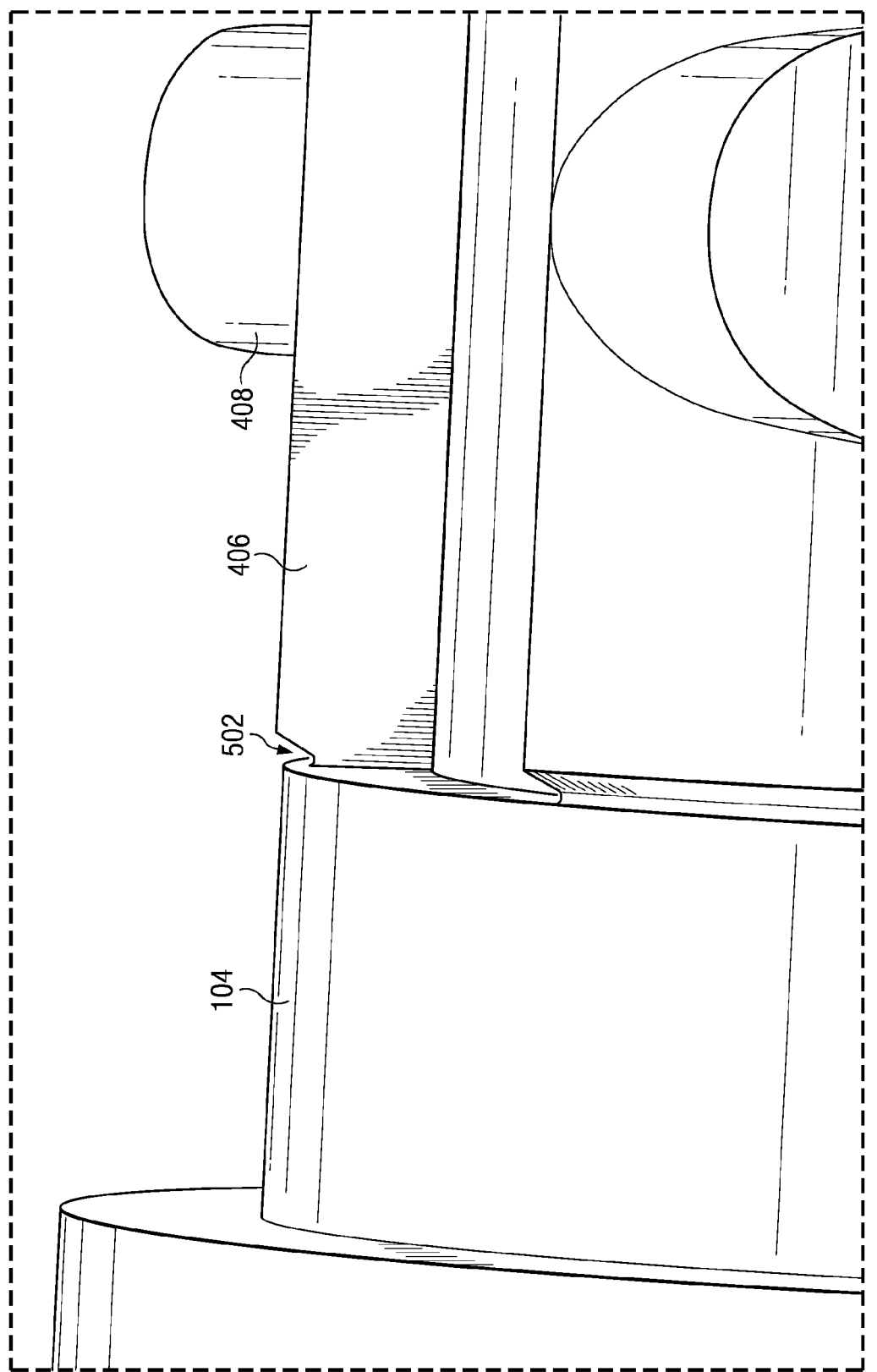
FIG. 5b shows an enlarged view of a break notch of a bone anchor in accordance with various embodiments.

FIG. 5a shows the bone anchor body 104, shown without the suture 102, suture plug 420, and rod 412 for simplicity. A region of reduced cross-sectional thickness, defined by a break notch 502 and the longitudinal bore 415, create the weakened connection that facilitates the controlled separation of the bone anchor body 104 from the retention member 406. This connection is almost circumferentially continuous, interrupted by the suture cutout 410. FIG. 5b shows a detailed view of the region A of FIG. 5a. The break notch 502 can be more clearly seen between the bone anchor body 104 and the retention member 406, and said notch 502 effectively reduces the ultimate tensile strength of that particular cross section, hence creating a predictable location where dislocation or separation will occur. The break notch 502 may be a continuous line, stopping and starting at the suture cutout 410, and may be disposed approximately parallel to or adjacent to the circumference of the anchor body 104. To cause the separation, the suture plug rod 412 is first used to set the suture plug 420 in the longitudinal bore 415 to affect a suture lock. Once the suture lock is achieved, the rod 412 continues to drive the suture plug 420 against the cross-pin 404 until the axial forces exceed the strength of the connection between the body 104 and member 406, weakened by the presence of the break notch 502. The bone anchor body 104 then separates from the retention member 406, which is retained by the grasping member 166, engaged by the lugs 408. FIG. 5c shows the bone anchor body 104 after being separated from the retention member 406, or how the bone anchor body 104 would appear after implantation into bone and removal of the retention member 406 by the applicator system 150. The bone anchor body 104 is shown without a length of suture 102 and suture plug 420 for simplicity.

Figure 6A:
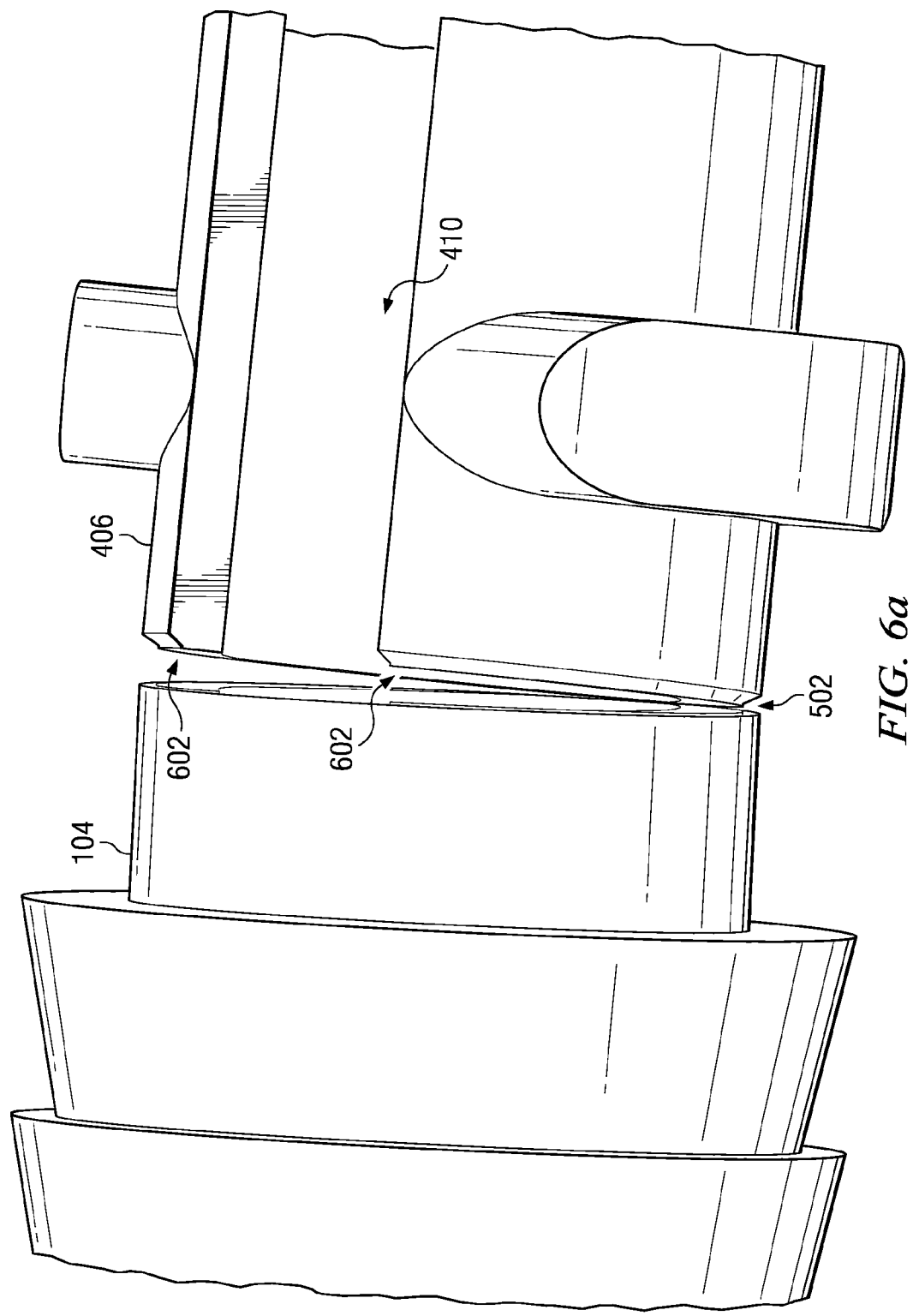
FIG. 6a shows a bone anchor during off-axis separation from a retention member in accordance with various embodiments.

FIG. 6a shows the bone anchor body 104 being detached from the retention member 406. In some cases, the separation occurs at initiation sites 602 of the break notch 502. This is due to the suture cutout 410, which is partially disposed along the break notch 502, and causes the initiation sites 602 to be the weakest area of the break notch 502.

Figure 6B:
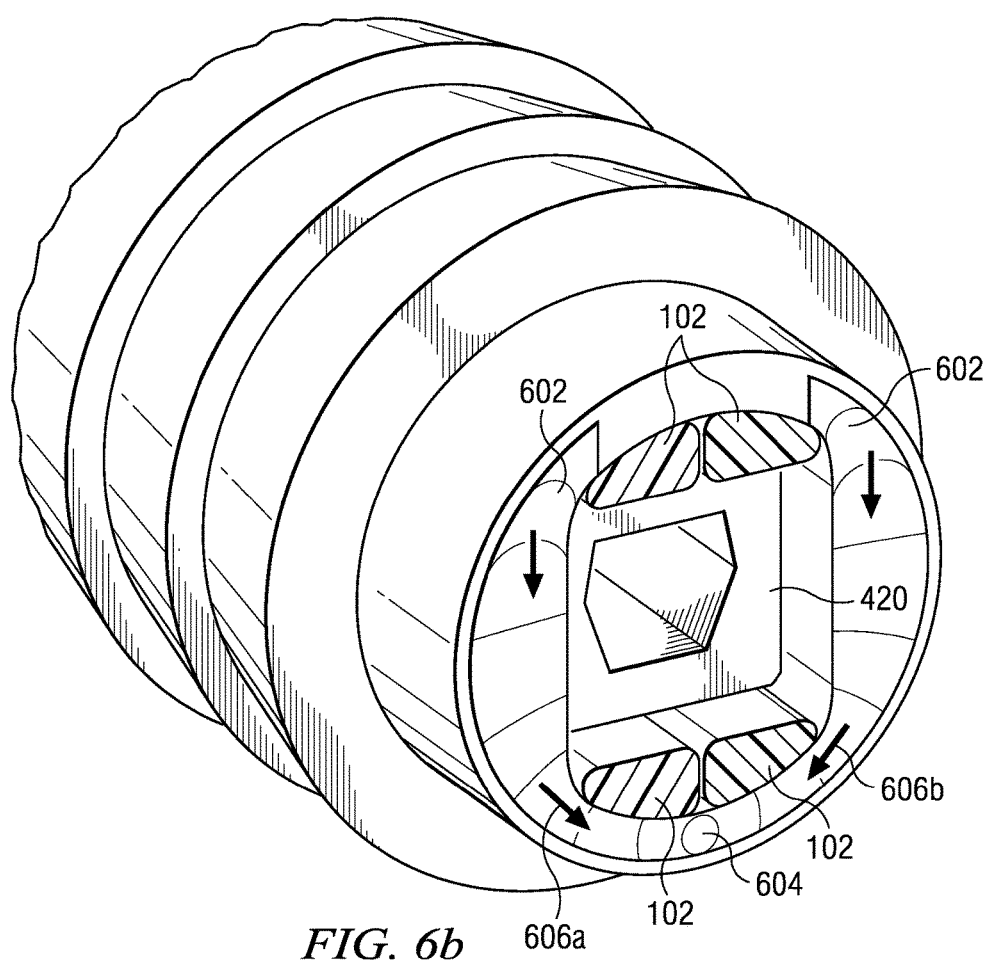
FIG. 6b shows exemplary force vectors generated around a bone anchor during off-axis separation from a retention member in accordance with various embodiments.

FIG. 6b shows the propagation of loading as the separation progresses from initiation sites 602, travelling circumferentially around the bone anchor body 104 to a point 604 that is approximately equidistant and opposite from the initiation sites 602. When separation between the bone anchor body 104 and the retention member 406 begins, the suture plug longitudinal tensile load leads to forces on the bone anchor body 104 that are largely also in the longitudinal axis. However, as the separation progresses around the circumference of the break notch 502 toward the point 604, loading on the anchor body 104 becomes asymmetric as the anchor body 104 breaks away and is amplified in the radial direction, resulting in a large amount of radial stress at the final area of attachment (e.g., point 604). The suture plug 420 wedging the suture 102 against the inner wall of the longitudinal bore 415 places additional radial stress on the bone anchor body 104. Thus, as the force vector caused by separation of the bone anchor body 104 from the retention member 406 shifts (i.e., from the longitudinal direction to the radial direction), radial stress increases and additionally begin to act on a shrinking area (e.g., point 604). This increase in stress combined with the potential structural effects of the two colliding fracture fronts 606a, 606b may result in an overloading, which may cause a longitudinal fracture to propagate along the bone anchor body 104.

Figure 6C:
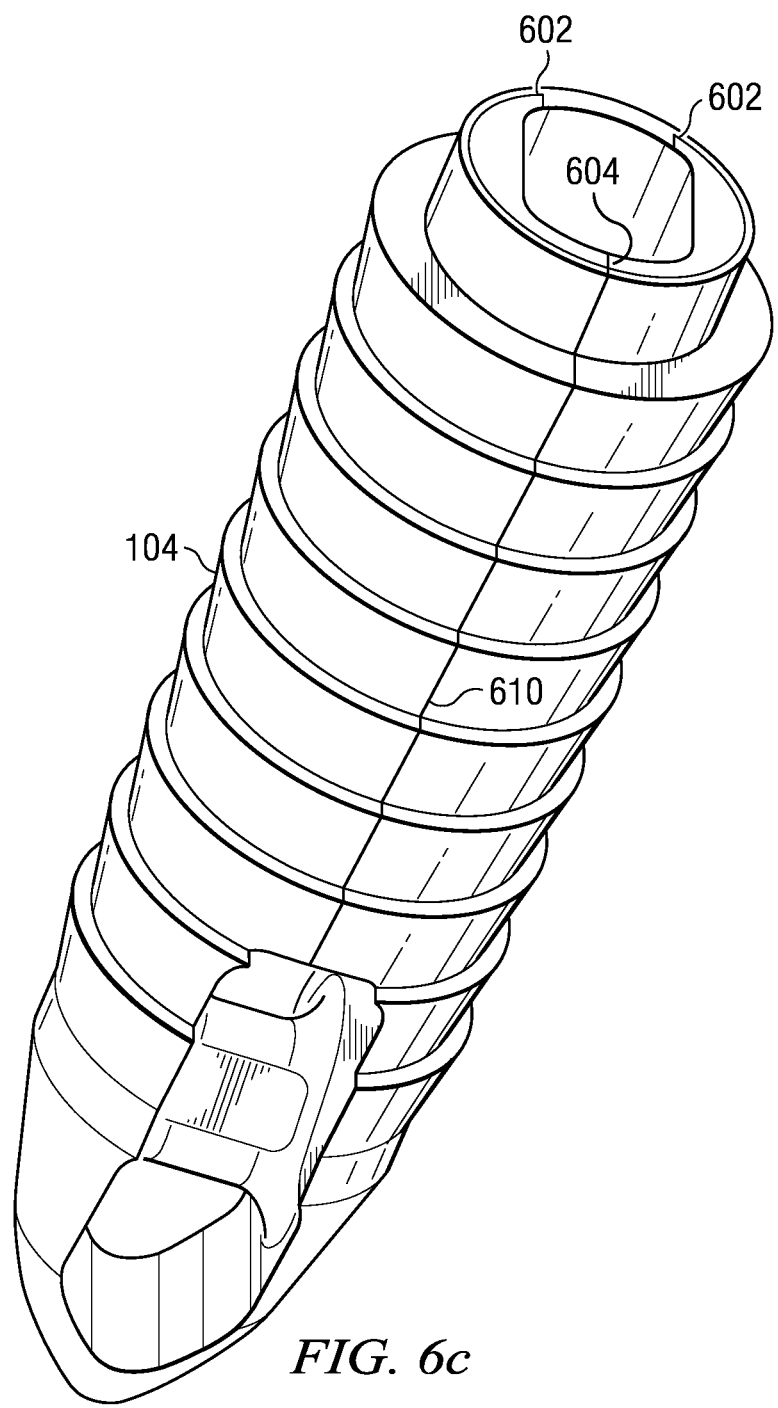
FIG. 6c shows an exemplary failure of a bone anchor resulting from the force vectors generated during off-axis separation from a retention member.

FIG. 6c shows a longitudinal fracture 610 along the bone anchor body 104. The longitudinal fracture 610 originates at the point 604, which, as explained above, is roughly equidistant and opposite from the separation initiation sites 602. Such a fracture may render the bone anchor body 104 unusable for anchoring a suture or may reduce the usable life of the bone anchor body 104.

Figure 7A:
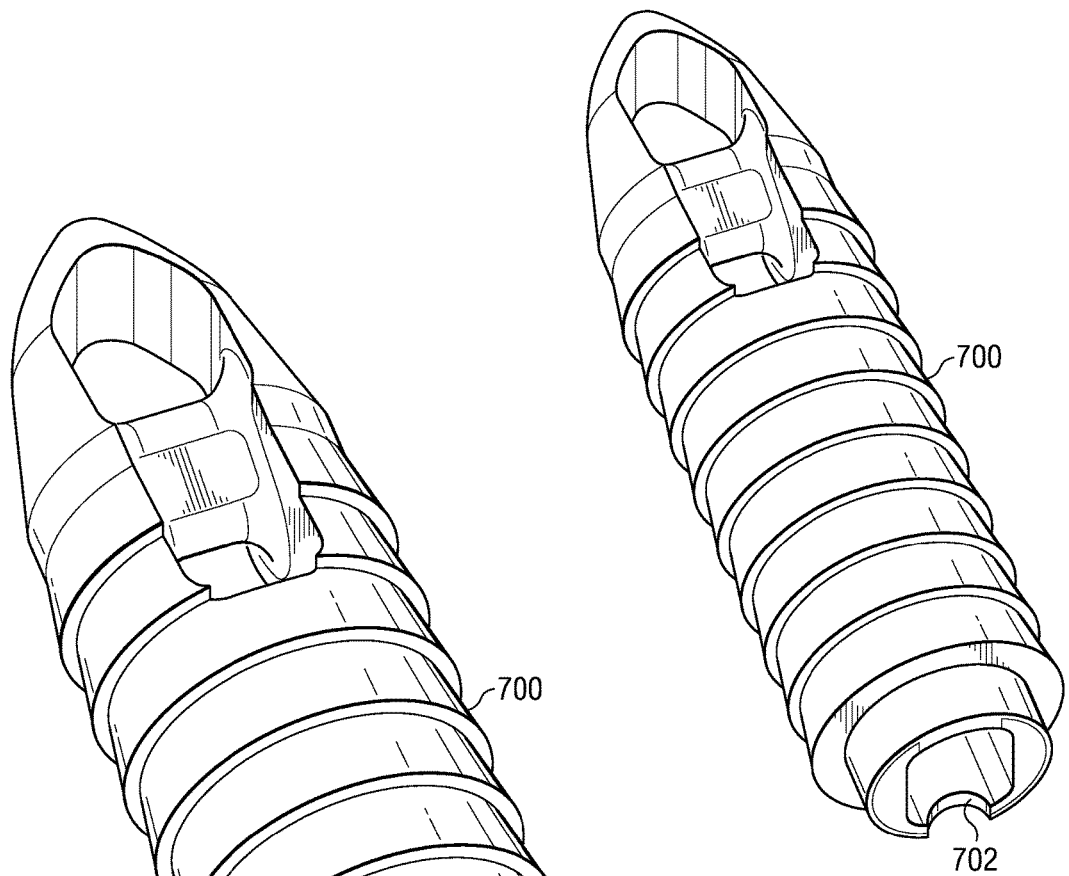
FIG. 7a shows a bone anchor and a retention member with a relief feature in accordance with various embodiments.

FIG. 7a shows a bone anchor body 700 with the retention member 406 attached, comprising a relief feature 702 in accordance with various embodiments. The relief feature 702 is positioned along the break notch 502 approximately equidistant and opposite from the separation initiation sites 602. Relief feature 702 is operable to interrupt the circumferentially disposed break notch 502 so as to disrupt and alter the propagation of the fracture around the bone anchor body cross section. In some cases this disruption moves the point of stress to areas of larger cross sectional surface area or cross sectional thickness, and/or to multiple points, reducing any one point of stress. In some cases, the relief feature 702 comprises a hole centered on the break notch 502 and diametrically opposed to the suture cutout 410. Adding this relief feature 702 allows for either an offset separation initiating at points 602, or axial separation (described later).

Figure 7C:
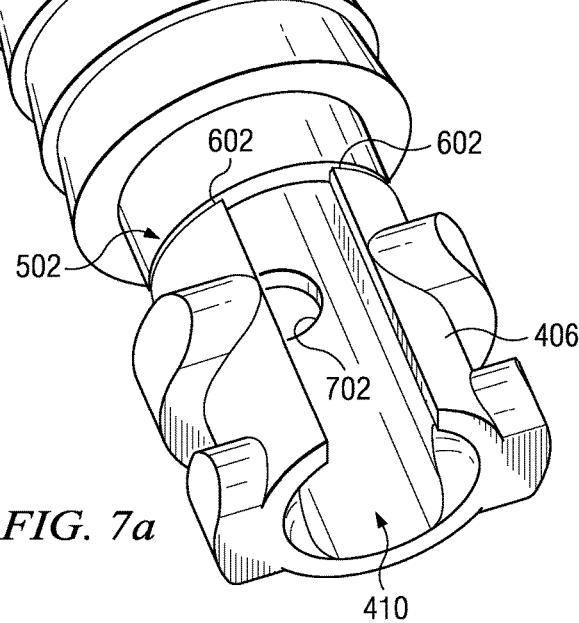
FIG. 7c shows a bone anchor with a relief feature after separation from a relief member in accordance with various embodiments.
Figure 7B:
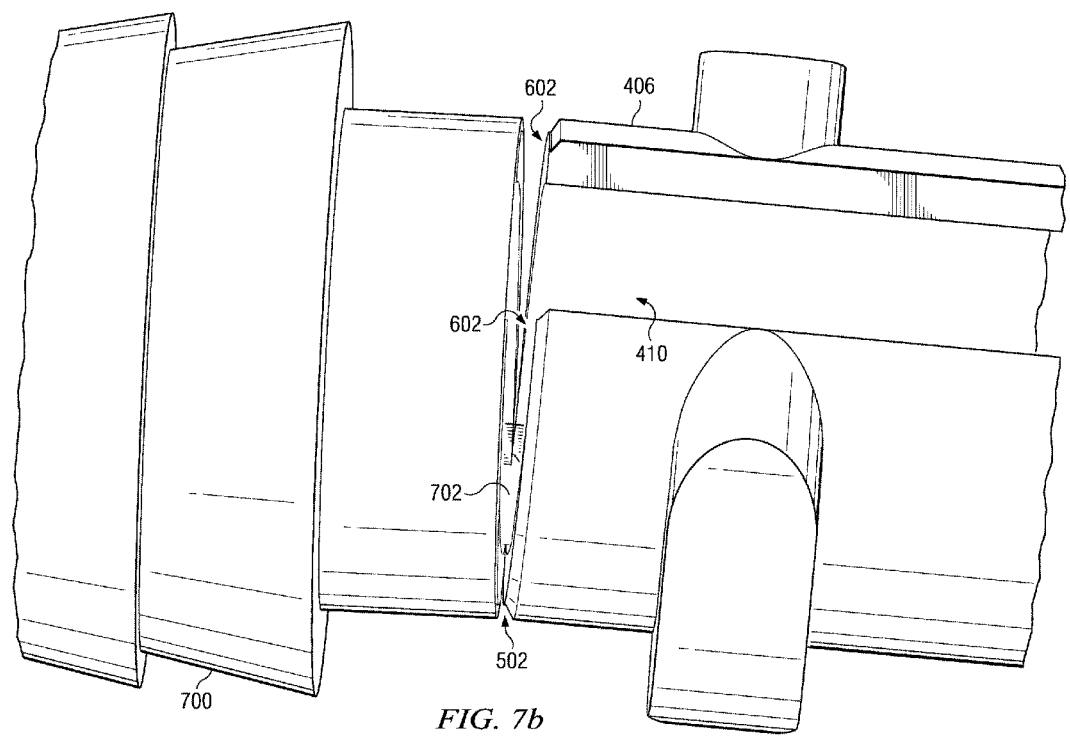
FIG. 7b shows a bone anchor and a retention member with a relief feature during off-axis separation in accordance with various embodiments.

FIG. 7b shows a bone anchor body 700, undergoing an off-axis detachment from the retention member 406, in accordance with various embodiments. In these cases, the separation may occur at initiation sites 602 of the break notch 502 as explained above. This is due to the suture cutout 410, which is in communication with the break notch, causing the initiation sites 602 to be one of the weaker areas of the break notch 502. The relief feature 702 is diametrically opposed to the suture cutout 410 and is approximately equidistant and opposite from the separation initiation sites 602. Stress may now propagate circumferentially around the cross section of the bone anchor body 700 and dissipate at or before relief feature 702.

FIG. 7c shows the bone anchor body 700 after being separated from the retention member 406, or how the anchor body 700 would appear after implantation into a bone cavity with removal of the retention member 406 by the applicator system 150. The anchor body 700 is shown without a length of suture 102 and suture plug 420 for simplicity. The relief feature 702 is positioned along the break notch 502 such that only a portion of the relief feature 702 remains after the bone anchor body 700 is separated from the retention member 406.

In the event of an offset detachment as illustrated in FIG. 7b, the fracture fronts intersect the relief feature 702 and dissipate prior to intersecting one another. Unlike the bone anchor body 104 where fracture fronts 606a, 606b come together at a point 604 and lead to a possible failure (e.g., fracture 610), the relief feature 702 enables a dissipation of forces that reduces or eliminates the chances of a failure in the bone anchor body 700.

Figure 7D:
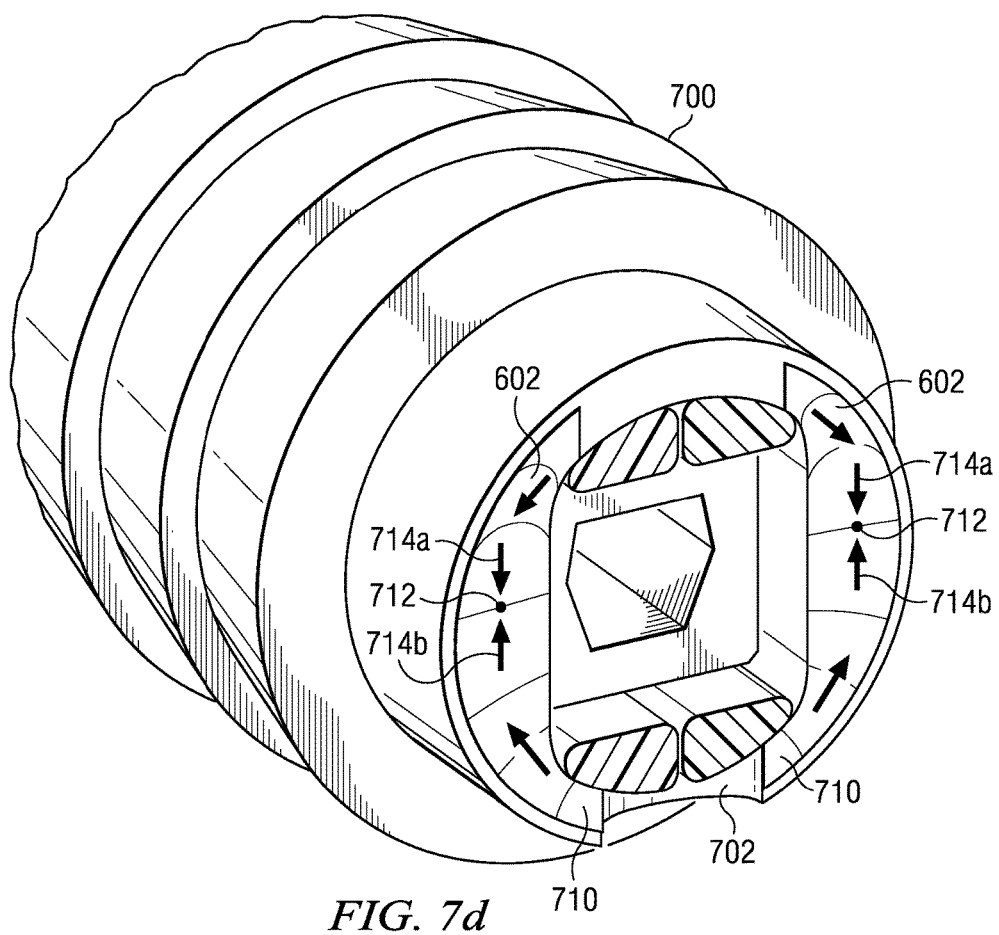
FIG. 7d shows exemplary force vectors generated around a bone anchor with a relief feature during axial separation from a retention member in accordance with various embodiments.

Additionally, as explained above with respect to FIG. 6a, the separation initiation sites 602 are located as such because of a structural weakness along the break notch 502 caused by the suture cutout 410. In some embodiments, or under axial separation, the relief feature 702 may cause a similar weakness along the break notch 502. FIG. 7d shows the propagation of loading as the separation progresses from initiation sites 602 as well as opposing initiation sites 710 to points 712 that are approximately circumferentially equidistant and opposite from the initiation sites 602, 710. The points 712 where fracture fronts 714a and 714b meet, are located in an area of the connection between the bone anchor body 700 and retention member 406 that has a larger wall thickness or cross sectional area, relative to the other portions of the connection. This wall thickness is defined by the break notch 502 and longitudinal bore 415. Thus, the potential structural effects of the colliding fracture fronts 714a, 714b is mitigated by the increased wall thickness, thereby reducing or eliminating the chances of a failure in the bone anchor body 700. Additionally there are two colliding fracture fronts, and not one larger combined front, effectively reducing the stress and chances of failure of the bone anchor body 700.

Figure 8:
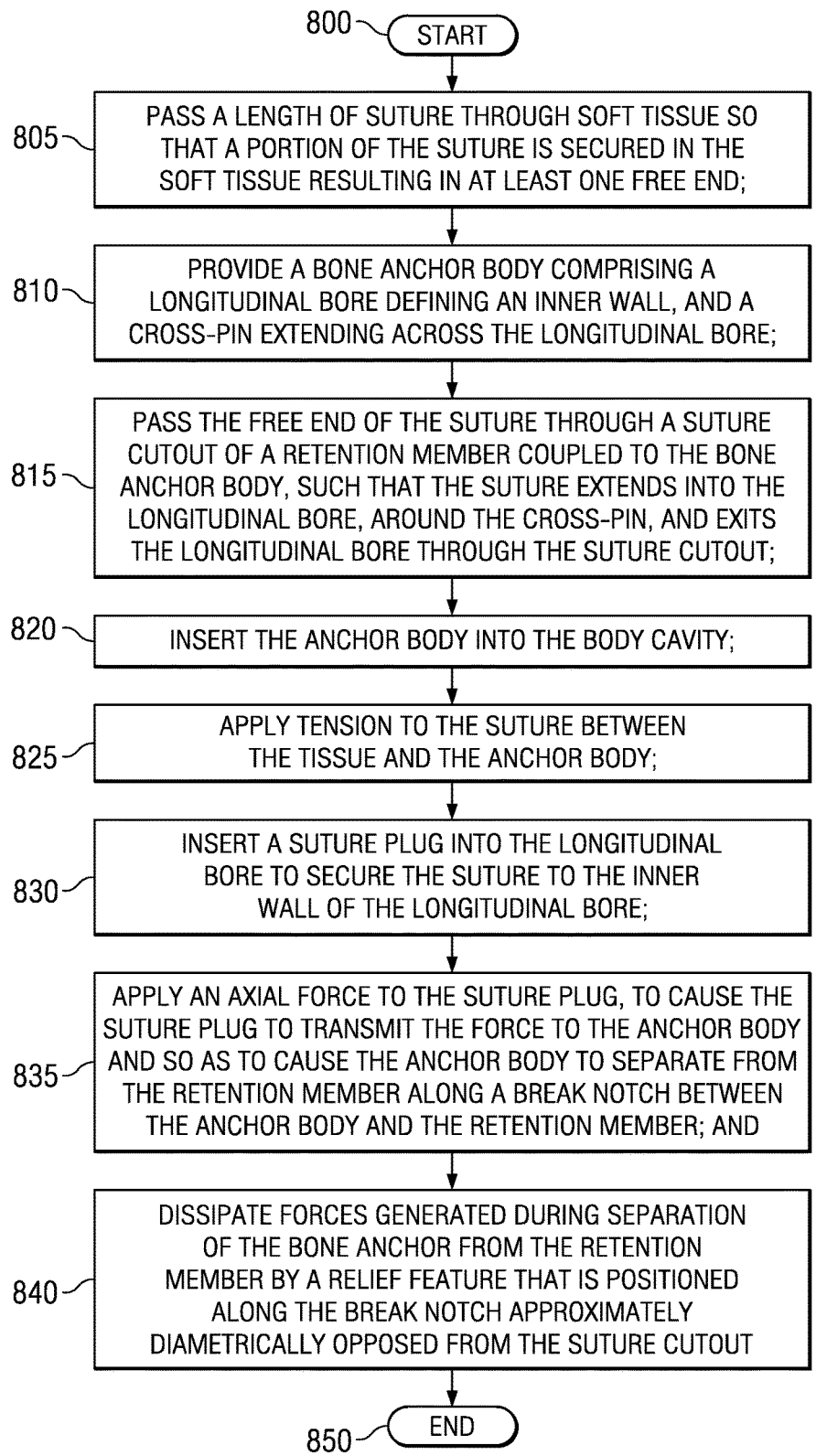
FIG. 8 shows a flow diagram of a medical procedure, using a system according to at least certain embodiments.

Referring now to FIG. 8, a method (800) for securing soft tissue with respect to a body cavity in accordance with at least some of the embodiments described herein is illustrated, including the steps of: passing a length of suture (805) through soft tissue so that a portion of the suture is secured in the soft tissue resulting in at least one free end of the length of suture, followed by providing a bone anchor body (810) comprising a longitudinal bore defining an inner wall, and a cross-pin extending across the longitudinal bore. The anchor body may be coupled to a retention member, which may be removably coupled to an applicator system. The free end of the suture may then be passed (815) through a suture cutout, disposed on the retention member, such that the suture extends through the suture cutout, into and along the longitudinal bore, around the cross-pin, and exits the longitudinal bore through the suture cutout. The anchor body may then be inserted (820) into the body cavity. Tension may then be applied (825) to the suture between the tissue and the bone anchor, so to better approximate the soft tissue to the anchor body and once the correct tension has been achieved, a suture plug may be inserted (830) into the longitudinal bore to secure the suture to the inner wall of the longitudinal bore. An axial force is then applied (835) to the suture plug, causing the suture plug to transmit the force to the bone anchor body and in turn cause the bone anchor body to separate from the retention member along a break notch located between the bone anchor body and the retention member. Forces generated during separation may then be dissipated (840) by a relief feature that is positioned along the break notch approximately diametrically opposed from the suture cutout. In some embodiments the relief feature is a circular hole disposed partially across both the bone anchor body and the retention member.

During the step of separation between the retention member and the bone anchor, separation initiation may occur at the suture cutout only and propagating forces may travel circumferentially and dissipate at both sides of the relief feature. Alternatively, during the step of separation, initiates may occur simultaneously at the suture cutout and the relief feature, and propagating forces may travel circumferentially and meet at a two points approximately equidistant between the relief feature and the suture cutout.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. As another example, although the relief feature is shown to be approximately circular, the relief feature could take a number of shapes while allowing stress dissipation in accordance with various embodiments. Accordingly, the scope of protection is not limited to the embodiments described herein, but is only limited by the claims that follow, the scope of which shall include all equivalents of the subject matter of the claims.

What is claimed is:

1. A knotless suture anchoring system for anchoring a length of suture with respect to a body cavity, comprising:
    a bone anchor body comprising at least one rigid anchoring structure to secure the anchor body within the body cavity, the anchor body further comprising a longitudinal bore and a cross-pin extending laterally through the longitudinal bore;
    a retention member coupled to the anchor body;
    a suture plug for placement in the longitudinal bore to frictionally secure at least one length of suture within the longitudinal bore;
    a break notch disposed between the anchor body and the retention member, wherein the break notch and the longitude bore define a relatively low ultimate tensile strength connection between the retention member and bone anchor configured to facilitate a controlled fracture and separation of the anchor body from the retention member; and
    a suture cutout disposed on the retention member and in communication with the break notch, operable so that a suture may enter the longitudinal bore and exit the longitudinal bore after being passed around the cross-pin; and
    a relief feature positioned through the relatively low ultimate tensile strength connection wherein the relatively low ultimate strength connection defines a circumferential connection, interrupted by the relief feature.

2. The knotless suture anchoring system of claim 1 wherein the relief feature comprises a hole disposed partially in the bone anchor body and partially in the retention member.

3. The knotless suture anchoring system of claim 1 wherein the retention member comprises one or more lugs to be engaged by a grasping member.

4. The knotless suture anchoring system of claim 1, wherein the circumferential connection between the retention member and bone anchor is further interrupted by the suture cutout.

5. The knotless suture anchoring system of claim 1 wherein the anchor body is constructed from a PEEK material.

6. The knotless suture anchoring system of claim 1, the relatively low ultimate strength connection having a variable cross section thickness is largest at points that are circumferentially equidistant between the relief feature and suture cutout.

7. The knotless suture anchoring system of claim 1 wherein a suture plug distal tip is configured so as to engage and apply a load upon the cross-pin and thereby the bone anchor, so as to cause the bone anchor body to separate from the retention member.

8. The knotless suture anchoring system of claim 7 further comprising a suture plug driver rod, slidably disposed within the retention member and in communication with the suture plug, said driver rod operable to place the suture plug within the longitudinal bore and apply an axial force to the plug, so as to cause the bone anchor body to separate from the retention member.

9. The knotless suture anchoring system of claim 1 further comprising an applicator system for inserting and manipulating the bone anchor, comprising;
    a grasping member for grasping the retention member and;
    a driving rod coaxially located within the grasping member and retention member, operable to load the suture plug within the bone anchor bore.

10. The knotless suture system of claim 1, wherein the relief feature is disposed so as to define at least one relief feature fracture initiation site on the relatively low ultimate tensile strength connection.

11. A knotless suture anchoring system for anchoring a length of suture with respect to a body cavity, comprising:
    a bone anchor body applicator;
    a bone anchor body comprising at least one rigid anchoring structure to secure the bone anchor body within the body cavity, the bone anchor body further comprising a longitudinal bore and a cross-pin extending laterally through the longitudinal bore;
    a retention member coupled to the bone anchor body via an annular connection and engaged with the bone anchor body applicator;
    a suture plug for placement in the longitudinal bore to frictionally secure a suture to the inner wall of the longitudinal bore;
    a suture plug driver rod, in communication with the suture plug and disposed coaxially within the retention member;
    a break notch circumferentially disposed around the annular connection, configured so as to reduce a cross sectional thickness of the annular connection and facilitate controlled fracture and separation of the bone anchor body from the retention member; and a suture cutout disposed on the retention member and in communication with the break notch, operable so that a suture may enter and exit the longitudinal bore after being passed around the cross-pin without interrupting the motion of the driver rod; and a relief feature disposed through the annular connection, so as to interrupt the annular connection and alter stress propagation around the annular connection during fracture and separation.

12. The knotless suture anchoring system of claim 11, wherein the relief feature comprises a transverse hole relative to the longitudinal bore, disposed partially in the bone anchor and partially in the retention member.

13. The knotless suture anchoring system of claim 11, wherein the annular connection between the retention member and bone anchor is further interrupted by the suture cutout.

14. The knotless suture anchoring system of claim 13 wherein the cross sectional thickness is variable around the annular connection and wherein the cross sectional thickness is largest at the locations that are circumferentially equidistant between the relief feature and suture cutout.

15. The knotless suture system of claim 1 or 11 wherein the relief feature is diametrically opposed the suture cutout.

16. The knotless suture system of claim 1 or 11, wherein the suture cutout defines at least one fracture initiation site on the relatively low ultimate tensile strength connection.

17. The knotless suture system of claim 16 wherein the relief feature is disposed so as to be circumferentially spaced away from the at least one fracture initiation site.

* * * * *